United States Patent [19]

Shih

[11] 4,238,275
[45] Dec. 9, 1980

[54] PYROCATECHOL-AMINE-WATER SOLUTION FOR THE DETERMINATION OF DEFECTS

[75] Inventor: Kwang K. Shih, Yorktown Heights, N.Y.

[73] Assignee: International Business Machines Corporation, Armonk, N.Y.

[21] Appl. No.: 974,586

[22] Filed: Dec. 29, 1978

[51] Int. Cl.³ .......................................... H01L 21/306
[52] U.S. Cl. .................................. 156/626; 156/662; 252/79.1
[58] Field of Search ............... 156/626, 636, 645, 647, 156/657, 662, 903, 653; 252/79.1, 79.4, 79.5

[56] References Cited
PUBLICATIONS

J. Electrochem. Soc.: Solid State Science, A Water-Amine-Complexing Agent System for Etching Silicon by R. M. Finne et al, Sep. 1967, pp. 965-970.
J. Electrochem. Soc.: Solid State Science, Substrate Surface Preparation and its Effect on Epitaxial Silicon by P. Rai-Chondhury, Jul. 1971, pp. 1183-1189.
IBM Technical Disclosure Bulletin, vol. 19, No. 9, Feb. 1977, Controlled Anisotropic Etching of Single Crystal Silicon by E. Bassous, pp. 3623-3624.
SCP and Solid State Technology, Slip and Bowing Control by Advanced Etching Techniques by Charles Wenzel, Aug. 1967, pp. 40-44.

Primary Examiner—William A. Powell
Attorney, Agent, or Firm—Hansel L. McGee

[57] ABSTRACT

The invention is directed to a novel method for detecting surface damage to polished silicon wafers. For very fine defects and scratches an oxidation step is used. The oxide is removed and the wafer is treated in an etch solution containing pyrocatechol, ethylene diamine and water. The defects are detectable by the naked eye.

15 Claims, 3 Drawing Figures

PYROCATECHOL-AMINE-WATER SOLUTION FOR THE DETERMINATION OF DEFECTS

BACKGROUND OF THE INVENTION

In the preparation of silicon devices, more particularly non-electronic devices, there is a need to remove surface damage on the silicon wafers used in device preparation. Mechanical and/or chemical polishing techniques are used to remove these surface damages. However, surfaces may be damaged as a result of polishing. It becomes necessary therefore to inspect the surfaces for damages after polishing and prior to device fabrication.

These surface damages, in the case of non-electronic applications such as ink jet nozzles, can lead to devices having poorly defined geometries. For example, in the fabrication of ink jet nozzles it is desired to obtain square holes upon etching. Surface damages, however, can cause the holes to be of different geometries, e.g., elliptical, rectangular etc. Additionally, these surface damages can cause scalloping on the walls of the ink jet nozzle where smooth walls are desired. Non-uniformity in hole sizes also arise as a result of these surface damages. In the case of electronic applications these surface damages cause reduced yields, increased shorts, non-uniformity in electrical properties and variations in dielectric breakdown thresholds.

Methods using etchants to detect dislocations and other lattice defects are known. Etchants used for such purpose are described in the publication to F. Secco d'Aragona entitled "Dislocation Etch for (100) Planes in Silicon", J. Electrochem. Soc. Solid-State Science and Technology p. 945, July 1972. The reference teaches the use of an alkali dichromate and hydrofluoric acid etch for revealing dislocation and other lattice defects in (100) planes of silicon. Similarly, the reference to D. C. Schimmel entitled "A Comparison of Chemical Etches for Revealing <100> Silicon Crystal Defects", J. Electrochem. Soc. Solid-State Science and Technology, p. 734, May 1976 compares the effect of etchants and their abilities to detect dislocations and other lattice defects. Specifically etchants such as the Chromate-HF of the above reference and variants thereof and HF—HNO$_3$ and variants, are considered. Non of these references are concerned with the detection of non-structural defects caused by polishing the surfaces of silicon wafers.

SUMMARY OF THE INVENTION

The present invention is directed to a method for detecting surface defects on the surface of silicon devices which are due to polishing these surfaces. More specifically the invention relates to a method for detecting surface defects which are visibly detected without the use of microscopy. The invention is characterized by the use of a ternary etchant consisting of pyrocatechol, amine and water and can be described by the following sequence of steps:

(a) cleaning silicon wafers in an appropriate cleaning solution;

(b) growing a SiO$_2$ film on said cleaned silicon wafers;

(c) immersing the silicon wafers having SiO$_2$ thereon in buffered hydrofluoric acid for a time sufficient to remove said SiO$_2$;

(d) rinsing the silicon wafers in water;

(e) immersing said silicon wafers in a heated pyrocatecholethylene-diamine-water etching solution for about five minutes;

(f) successively rinsing said wafers in water, buffered HF and water; and thereafter;

(g) visually inspecting the surfaces for etch pits and scratches.

The type of etchants encompassed in the present invention are known. They are described in a publication to R. M. Finne and D. L. Klein entitled "A Water-Amine-Complexing Agent System for Etching Silicon", J. Electrochem. Soc. Solid State Science, p. 965, September 1967. The publication primarily teaches that pyrocatechol-amine-water solutions can be used effectively to etch silicon. Additionally it teaches that the etchants can be used to detect defects in oxide films deposited on the surface of silicon. There is no teaching therein however, to use the etchants to detect surface defects caused by polishing of the surface of silicon wafers.

DETAILED DESCRIPTION OF THE INVENTION

Figure 1A:
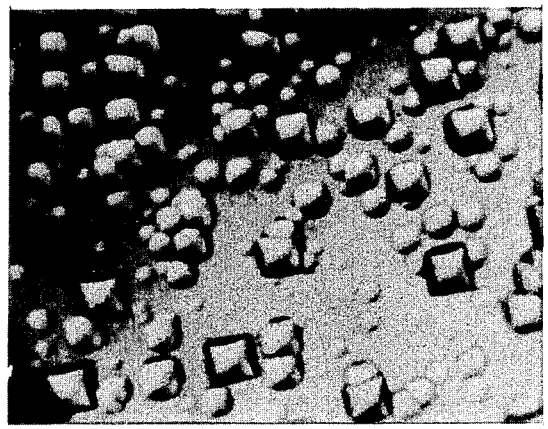
FIG. 1 (a,b,c) depicts the defects on the surface of a silicon wafer treated with pyrocatechol-amine-water etch, Secco etch, and Sirtl etch respectively.

In the conventional way of making silicon wafers, slices cut from ingots are first mechanically lapped to make them flat and acid etched to remove damage, then chem-mechanical polished to obtain smooth and damage free surfaces. In practice, the polished surfaces may not be free of surface damages. In general, the prior art, in order to detect surface damage, etched the wafer in Sirtl or Secco etches described in the above-mentioned publications. These etches not only reveal the surface damage as microscopically small pits but also reveal other defects such as swirl defects which are grow-in defects as microscopically small pits.

What has been discovered here is that a pyrocatecholethylene-diamine-water solution developed by Finne and Klein, described in the publication aforementioned, provides an excellent etching solution for revealing surface damages. This etch is found to reveal surface damage large enough to be detected with the naked eye and easily counted.

For purpose of this invention the etching solution is prepared by dissolving from about 100 gm to about 120 grams of pyrocatechol, from about 750 ml to about 1000 ml of ethylene diamine in from about 120 ml to about 240 ml of water.

The solution is maintained at a temperature of from about 90° C. to about 120° C. during the etching procedure. The wafer to be examined is immersed in the etchant solution for from about 2 minutes to about 10 minutes. In a preferred embodiment of the invention the etchant is comprised of 120 gm of pyrocatechol, 750 ml ethylene diamine and 240 ml water. The solution is maintained at a temperature of about 118° C. The wafer is immersed in such etchant for about 5 minutes.

In practice the method for determining very fine defects, i.e., defects measuring less than ½ micron, the following procedure is carried out:

(a) growing an oxide film on the surface of a cleaned silicon wafer;

(b) immersing said silicon wafer in buffered hydrofluoric acid to remove said oxide film from the surface of said silicon wafer;

(c) rinsing said oxide free wafers in water;

(d) immersing said rinsed wafers in a pyrocatechol-amine-water etch solution;

(e) rinsing said so treated wafer in water and thereafter (f) inspecting said wafer's surface for defects.

Oxide films are grown on the polished and clean silicon wafers to accentuate very fine defects, i.e. defects measuring less than $\frac{1}{2}\mu$. The oxide films may be grown thermally by conventional methods. The thickness of the oxide films can be varied from about 1000 Å to about 5000 Å. It should be realized that where surface defects exceeds $\frac{1}{2}\mu$ in size, the oxide forming step is not needed. However, where the defect size is less than $\frac{1}{2}\mu$, oxide formation is necessary since without this step the defects will not be readily discernible.

The silicon wafers can be cleaned in standard and conventional silicon cleaning solutions. For example, the well known Hwang solution can be used.

In a preferred embodiment a wafer was subjected to thermal oxidation until a $SiO_2$ film of about 5000 Å was grown on its surface. The wafer was then immersed in buffered hydrofluoric acid for about 10 minutes until the $SiO_2$ film was dissolved or etched away. After rinsing the wafer in water it was then immersed in an etchant comprising 120 gm of pyrocatechol and 750 ml ethylene diamine dissolved in 240 ml of water heated at about 118° C. The wafer remained immersed for about 5 minutes and again rinsed in water.

When it is determined that the defects are greater than $\frac{1}{2}\mu$ in size the above procedure can be used however the oxidation step need not be followed.

Figure 1B:
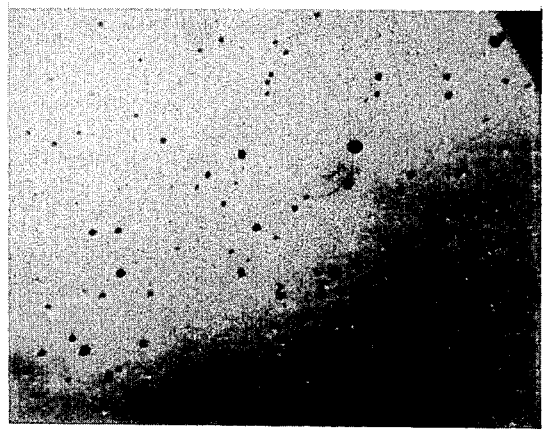
Figure 1C:
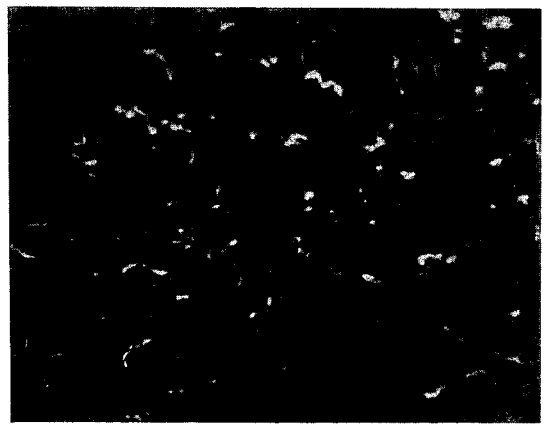

Inspection of the treated wafers can be made by the naked eye or by microscope. Generally where etch pit density is greater than 1 cm $^{-2}$ or if any scratch is observed in the area approximately 0.8 R (radius) from the center of the wafer, the wafer is rejected. FIG. 1a shows the defects on the surface of a silicon wafer treated by the method of this invention. It is clear that defects detected by the present method can be readily seen by visual inspection whereas when similar wafers treated by prior art methods, e.g., using Secco and Sirtl etches, the defects are at best difficult to observe with the naked eye. Secco and Sirtl treated wafers are shown in FIGS. 1b and 1c respectively. FIG. 1c is magnified by 100.

The wafers were treated in Secco and Sirtl etchants according to the precedures described in the aforementioned publication to D. G. Schimmel entitled "A Comparison of Chemical Etches for Revealing <100> Silicon Crystal Defects", J. Electrochem. Soc., Solid-State Science and Technology, p. 734, May 1976. The procedures described therein are incorporated here by reference.

Having thus described may invention, what I claim as new, and desire to secure by Letters Patent is:

1. A non-microscopic method for visually detecting surface damage on polished silicon wafer surfaces including the steps of:
   (a) growing a $SiO_2$ film on the surface of said polished silicon wafer surfaces;
   (b) immersing said $SiO_2$ covered silicon wafer in buffered HF for a time sufficient to remove said $SiO_2$ film;
   (c) rinsing said $SiO_2$ free wafer in water,
   (d) immersing said $SiO_2$ free wafer in a etch solution comprising pyrocatechol, ethylene diamine and water for a time sufficient to cause defects in the surface of said wafer to appear, thereafter
   (e) rinsing said wafer and inspecting the surface of said wafer for etch pits and scratches.

2. A non-microscopic method for visually detecting surface damage on polished silicon wafer surfaces according to the method of claim 1 wherein said etch solution is comprised of from about 100 gms to about 120 gms of pyrocatechol, from about 750 ml to about 1000 ml of ethylene diamine and from about 120 ml to about 240 ml of water.

3. A non-microscopic method for visually detecting surface damage on polished silicon wafer surfaces according to the method of claim 2 wherein said etch solution is comprised of 120 gms of pyrocatechol, 750 ml of ethylene diamine and 240 ml of water.

4. A non-microscopic method for visually detecting surface damage on polished silicon wafer surfaces according to the method of claim 3 wherein said etch solution is maintained at a temperature in the range of from about 90° C. to about 120° C.

5. A non-microscopic method for visually detecting surface damage on polished silicon wafer surfaces according to the method of claim 4 wherein said temperature is maintained at 118° C.

6. A non-microscopic method for visually detecting surface damage on polished silicon wafer surfaces according to the method of claim 4 wherein said $SiO_2$ covered silicon wafer is immersed in said buffered HF for from about 10 to about 30 minutes.

7. A non-microscopic method for visually detecting surface damage on polished silicon wafer surfaces according to the method of claim 6 wherein said $SiO_2$ covered silicon wafer is immersed in said buffered HF for about 10 minutes.

8. A non-microscopic method for visually detecting surface damage on polished silicon wafer surfaces according to the method of claim 7 wherein said $SiO_2$ free silicon wafer is immersed in said etch solution for from about 2 minutes to about 10 minutes.

9. A non-microscopic method for visually detecting surface damage on polished silicon wafer surfaces according to the method of claim 8 wherein said $SiO_2$ free silicon wafer is immersed in said etch solution for about 5 minutes.

10. A non-microscopic method for visually detecting surface damage on polished silicon wafer surfaces where said surface damage is greater than $\frac{1}{2}$ micron in size including the steps of:
    (a) immersing said silicon wafer in an etch solution comprising from about 100 gms to about 120 gms of pyrocatechol, from about 750 ml to about 1000 ml of ethylene diamine and 240 ml of water for a time sufficient to cause surface defects on rinsing the surface of said wafer to appear; and thereafter
    (b) rinsing said wafer in water and inspecting the surface of said wafer for etch pits and scratches.

11. A method according to the method of claim 10 wherein said etch solution is comprised of 120 gms of pyrocatechol, 750 ml of ethylene diamine and 240 ml of water.

12. A method according to the method of claim 11 wherein said etch solution is maintained at a temperature of from about 90° C. to about 120° C.

13. A method according to the method of claim 12 wherein said etch solution is maintained at a temperature of 118° C.

14. A method according to the method of claim 13 wherein said silicon wafer is immersed in said etch solution for from about 2 minutes to about 10 minutes.

15. A method according to the method of claim 14 wherein said silicon wafer is immersed in said etch solution for about 5 minutes.

* * * * *